United States Patent
Modak et al.

(10) Patent No.: US 8,906,401 B2
(45) Date of Patent: Dec. 9, 2014

(54) ANTIMICROBIAL MEDICAL DEVICES CONTAINING CHLORHEXIDINE FREE BASE AND SALT

(71) Applicant: The Trustees of Columbia University in the City of New York, New York, NY (US)

(72) Inventors: Shanta M. Modak, River Edge, NJ (US); Lester A. Sampath, Nyack, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/758,686

(22) Filed: Feb. 4, 2013

(65) Prior Publication Data
US 2013/0150452 A1 Jun. 13, 2013

Related U.S. Application Data

(60) Continuation of application No. 11/946,622, filed on Nov. 28, 2007, now Pat. No. 8,383,143, which is a division of application No. 09/746,670, filed on Dec. 22, 2000, now Pat. No. 7,329,412.

(51) Int. Cl.
- *A61F 2/02* (2006.01)
- *A61L 15/44* (2006.01)
- *A61L 29/16* (2006.01)
- *A61L 27/54* (2006.01)
- *A61L 31/16* (2006.01)

(52) U.S. Cl.
CPC ............... *A61L 31/16* (2013.01); *A61L 15/44* (2013.01); *A61L 2300/404* (2013.01); *A61L 2300/206* (2013.01); *A61L 29/16* (2013.01); *A61L 27/54* (2013.01)
USPC .......................................................... 424/423

(58) Field of Classification Search
None
See application file for complete search history.

(56) References Cited

U.S. PATENT DOCUMENTS

| | | | |
|---|---|---|---|
| 3,566,874 A | 3/1971 | Shepherd et al. |
| 3,674,901 A | 7/1972 | Shepherd et al. |
| 3,695,921 A | 10/1972 | Shepherd et al. |
| 3,699,956 A | 10/1972 | Kitrilakis et al. |
| 3,705,938 A | 12/1972 | Hyman et al. |
| 3,987,797 A | 10/1976 | Stephenson |
| 4,024,871 A | 5/1977 | Stephenson |
| 4,054,139 A | 10/1977 | Crossley |
| 4,064,238 A | 12/1977 | Bocher et al. |
| 4,070,713 A | 1/1978 | Stockum |
| 4,143,109 A | 3/1979 | Stockum |
| 4,243,657 A | 1/1981 | Okumura et al. |
| 4,273,873 A | 6/1981 | Sugitachi et al. |
| 4,318,947 A | 3/1982 | Joung |
| 4,381,380 A | 4/1983 | LeVeen et al. |
| 4,432,766 A | 2/1984 | Bellotti et al. |
| 4,499,154 A | 2/1985 | James et al. |
| 4,539,234 A | 9/1985 | Sakamoto et al. |
| 4,563,485 A | 1/1986 | Fox et al. |
| 4,581,028 A | 4/1986 | Fox et al. |
| 4,592,920 A | 6/1986 | Murtfeldt |
| 4,597,108 A | 7/1986 | Momose |
| 4,603,152 A | 7/1986 | Laurin et al. |
| 4,605,564 A | 8/1986 | Kulla et al. |
| 4,612,337 A | 9/1986 | Fox et al. |
| 4,623,329 A | 11/1986 | Drobish et al. |
| 4,675,347 A | 6/1987 | Mochizuki et al. |
| 4,677,143 A | 6/1987 | Laurin et al. |
| 4,723,950 A | 2/1988 | Lee |
| 4,738,668 A | 4/1988 | Bellotti et al. |
| 4,769,013 A | 9/1988 | Lorenz et al. |
| 4,771,482 A | 9/1988 | Shlenker |
| 4,853,978 A | 8/1989 | Stockman |
| 4,919,837 A | 4/1990 | Gluck |
| 4,925,668 A | 5/1990 | Khan et al. |
| 4,956,170 A | 9/1990 | Lee |
| 4,994,047 A | 2/1991 | Walker et al. |
| 4,999,210 A | 3/1991 | Solomon et al. |
| 5,013,306 A | 5/1991 | Solomon et al. |
| 5,013,717 A | 5/1991 | Solomon et al. |
| 5,019,096 A | 5/1991 | Fox et al. |
| 5,024,232 A | 6/1991 | Smid et al. |
| 5,031,245 A | 7/1991 | Milner |
| 5,033,488 A | 7/1991 | Curtis et al. |
| 5,059,416 A | 10/1991 | Cherukuri et al. |
| 5,061,254 A | 10/1991 | Karakelle et al. |
| 5,061,738 A | 10/1991 | Solomon et al. |
| 5,089,205 A | 2/1992 | Huang et al. |

(Continued)

FOREIGN PATENT DOCUMENTS

| | | |
|---|---|---|
| DE | 4140474 | 6/1993 |
| DE | 4240674 | 5/1996 |

(Continued)

OTHER PUBLICATIONS

U.S. Appl. No. 07/154,920, filed Feb. 11, 1998.
U.S. Appl. No. 08/103,087, filed Aug. 6, 1993.
U.S. Appl. No. 07/385,290, filed Jul. 25, 1989.
U.S. Appl. No. 07/258,189, May 19, 1989 Non-Final Office Action.
U.S. Appl. No. 07/258,189, Oct. 23, 1989 Response to Non-Final Office Action.
U.S. Appl. No. 07/258,189, Dec. 19, 1989 Final Office Action.
U.S. Appl. No. 07/258,189, Jun. 21, 1990 Response to Final Office Action.
U.S. Appl. No. 07/258,189, Aug. 24, 1990 Non-Final Office Action.
U.S. Appl. No. 07/258,189, Oct. 29, 1990 Response to Non-Final Office Action.

(Continued)

*Primary Examiner* — Carlos Azpuru
(74) *Attorney, Agent, or Firm* — Baker Botts, L.L.P.

(57) ABSTRACT

The present disclosure invention relates to medical devices treated with a solution comprising one or more solvents and a combination of chlorhexidine free base and a water-soluble chlorhexidine salt in a weight/weight ratio of between about 1:1 to about 1:5, preferably about 1:1.

6 Claims, No Drawings

(56) References Cited

U.S. PATENT DOCUMENTS

| | | |
|---|---|---|
| 5,091,442 A | 2/1992 | Milner |
| 5,102,401 A | 4/1992 | Lambert et al. |
| 5,133,090 A | 7/1992 | Modak et al. |
| 5,165,952 A | 11/1992 | Solomon et al. |
| 5,176,665 A | 1/1993 | Watanabe et al. |
| 5,180,605 A | 1/1993 | Milner |
| 5,196,205 A | 3/1993 | Borody |
| 5,200,194 A | 4/1993 | Edgren et al. |
| 5,208,031 A | 5/1993 | Kelly |
| 5,209,251 A | 5/1993 | Curtis et al. |
| 5,217,493 A | 6/1993 | Raad et al. |
| 5,236,422 A | 8/1993 | Eplett, Jr. |
| 5,261,421 A | 11/1993 | Milner |
| 5,263,930 A | 11/1993 | Ensminger |
| 5,334,588 A | 8/1994 | Fox, Jr. et al. |
| 5,335,373 A | 8/1994 | Dresdner, Jr. et al. |
| 5,357,636 A | 10/1994 | Dresdner, Jr. et al. |
| 5,403,864 A | 4/1995 | Bruch et al. |
| 5,420,197 A | 5/1995 | Lorenz et al. |
| 5,451,424 A | 9/1995 | Solomon et al. |
| 5,516,510 A | 5/1996 | Beilfuss et al. |
| 5,567,495 A | 10/1996 | Modak et al. |
| 5,591,442 A | 1/1997 | Diehl et al. |
| 5,616,338 A | 4/1997 | Fox et al. |
| 5,624,704 A | 4/1997 | Darouiche et al. |
| 5,688,516 A | 11/1997 | Raad et al. |
| 5,705,532 A | 1/1998 | Modak et al. |
| 5,707,366 A | 1/1998 | Solomon et al. |
| 5,708,023 A | 1/1998 | Modak et al. |
| 5,736,574 A | 4/1998 | Burnier et al. |
| 5,756,145 A | 5/1998 | Darouiche |
| 5,763,412 A | 6/1998 | Khan et al. |
| 5,772,640 A | 6/1998 | Modak et al. |
| 5,776,430 A | 7/1998 | Osbourne et al. |
| 5,830,488 A | 11/1998 | Suzuki et al. |
| 5,885,562 A | 3/1999 | Lowry et al. |
| 5,902,283 A | 5/1999 | Darouiche et al. |
| 5,928,671 A | 7/1999 | Domenico |
| 5,951,993 A | 9/1999 | Scholz et al. |
| 5,965,610 A | 10/1999 | Modak et al. |
| 5,980,477 A | 11/1999 | Kelly |
| 5,985,918 A | 11/1999 | Modak et al. |
| 5,985,931 A | 11/1999 | Modak et al. |
| 5,989,531 A | 11/1999 | Schamper et al. |
| 6,022,551 A | 2/2000 | Jampani et al. |
| 6,037,386 A | 3/2000 | Modak et al. |
| 6,040,347 A | 3/2000 | Cupferman et al. |
| 6,045,817 A | 4/2000 | Anathapadmanabhan |
| 6,083,208 A | 7/2000 | Modak et al. |
| 6,106,505 A | 8/2000 | Modak et al. |
| 6,107,261 A | 8/2000 | Taylor et al. |
| 6,136,771 A | 10/2000 | Taylor et al. |
| 6,187,327 B1 | 2/2001 | Stack |
| 6,204,230 B1 | 3/2001 | Taylor et al. |
| 6,211,243 B1 | 4/2001 | Johnson |
| 6,224,579 B1 | 5/2001 | Modak et al. |
| 6,261,271 B1 | 7/2001 | Solomon et al. |
| 6,323,171 B1 | 11/2001 | Fonsny et al. |
| 6,387,357 B1 | 5/2002 | Chopra et al. |
| 6,414,032 B1 | 7/2002 | Johnson |
| 6,416,546 B1 | 7/2002 | Kimura et al. |
| 6,416,548 B2 | 7/2002 | Chinn et al. |
| 6,420,431 B1 | 7/2002 | Johnson |
| 6,426,062 B1 | 7/2002 | Chopra et al. |
| 6,582,719 B2 | 6/2003 | Modak et al. |
| 6,626,873 B1* | 9/2003 | Modak et al. ............ 604/265 |
| 6,706,024 B2* | 3/2004 | Modak et al. ............ 604/265 |
| 6,719,991 B2 | 4/2004 | Darouiche et al. |
| 6,723,689 B1 | 4/2004 | Hoang et al. |
| 6,846,846 B2 | 1/2005 | Modak et al. |
| 6,872,195 B2 | 3/2005 | Modak et al. |
| 7,329,412 B2* | 2/2008 | Modak et al. ............ 424/423 |
| 7,537,779 B2* | 5/2009 | Modak et al. ............ 424/423 |
| 8,383,143 B2* | 2/2013 | Modak et al. ............ 424/423 |
| 2001/0010016 A1 | 7/2001 | Modak et al. |
| 2001/0024661 A1 | 9/2001 | Modak et al. |
| 2002/0022660 A1 | 2/2002 | Jampani et al. |
| 2002/0122876 A1 | 9/2002 | Modak et al. |
| 2002/0173775 A1 | 11/2002 | Modak et al. |
| 2003/0152644 A1 | 8/2003 | Modak et al. |
| 2004/0052831 A1 | 3/2004 | Modak et al. |
| 2004/0208908 A1 | 10/2004 | Modak et al. |
| 2005/0019431 A1 | 1/2005 | Modak et al. |
| 2005/0192547 A1 | 9/2005 | Modak et al. |
| 2006/0099237 A1 | 5/2006 | Modak et al. |

FOREIGN PATENT DOCUMENTS

| | | |
|---|---|---|
| EP | 0 313 302 | 4/1989 |
| EP | 0 328 421 | 8/1989 |
| EP | 0 379 271 | 7/1990 |
| EP | 0 472 413 | 2/1992 |
| EP | 0 604 848 | 7/1994 |
| EP | 0 663 212 | 7/1995 |
| EP | 0 882 461 | 12/1998 |
| FR | 2729050 | 7/1996 |
| GB | 2218617 | 11/1989 |
| JP | 11049625 | 2/1999 |
| WO | WO 90/01956 | 3/1990 |
| WO | WO 93/02717 | 2/1993 |
| WO | WO 93/06881 | 4/1993 |
| WO | WO 93/17746 | 9/1993 |
| WO | WO 96/22114 | 7/1996 |
| WO | WO 97/25085 | 7/1997 |
| WO | WO 00/37042 | 6/2000 |
| WO | WO 00/57933 | 10/2000 |
| WO | WO 03/000303 | 1/2003 |
| WO | WO 03/034994 | 5/2003 |
| WO | WO 03/066001 | 8/2003 |

OTHER PUBLICATIONS

U.S. Appl. No. 07/258,189, Dec. 14, 1990 Examiner's Amendment.
U.S. Appl. No. 07/258,189, Dec. 14, 1990 Notice of Allowance.
U.S. Appl. No. 07/258,189, Jan. 2, 1991 Examiner's Amendment.
U.S. Appl. No. 07/687,844, Aug. 11, 1992 Letter of Suspension-13 Examiner Initiated.
U.S. Appl. No. 07/687,844, Jun. 28, 1993 Miscellaneous Action with SSP.
U.S. Appl. No. 07/687,844, Aug. 2, 1993 Response after Non-Final Action.
U.S. Appl. No. 07/687,844, Mar. 17, 1994 Declaration of Interference.
U.S. Appl. No. 07/687,844, Jun. 22, 1994 Interference Decision on Priority—Adverse.
U.S. Appl. No. 07/687,844, Aug. 23, 1995 Interference Decision on Priority—Adverse.
U.S. Appl. No. 07/687,844, Aug. 23, 1995 Interference Decision on Priority—Favorable.
U.S. Appl. No. 07/687,844, Sep. 27, 1995 Non-Final Office Action.
U.S. Appl. No. 07/687,844, Dec. 26, 1995 Response to Non-Final Office Action.
U.S. Appl. No. 07/687,844, Feb. 27, 1996 Ex Parte Quayle Action.
U.S. Appl. No. 07/687,844, May 1, 1996 Response after Ex Parte Quayle Action.
U.S. Appl. No. 07/687,844, Jun. 3, 1996 Notice of Allowance.
U.S. Appl. No. 09/746,670, Jan. 10, 2003 Non-Final Office Action.
U.S. Appl. No. 09/746,670, Jul. 9, 2003 Response to Non-Final Office Action.
U.S. Appl. No. 09/746,670, Sep. 24, 2003 Final Office Action.
U.S. Appl. No. 09/746,670, Dec. 29, 2003 Response to Final Office Action.
U.S. Appl. No. 09/746,670, Feb. 13, 2004 Non-Final Office Action.
U.S. Appl. No. 09/746,670, Aug. 11, 2004 Response to Non-Final Office Action.
U.S. Appl. No. 09/746,670, Dec. 14, 2004 Notice of Allowance.
U.S. Appl. No. 09/746,670, Mar. 14, 2005 Request for Continued Examination.
U.S. Appl. No. 09/746,670, Jun. 17, 2005 Non-Final Office Action.
U.S. Appl. No. 09/746,670, Aug. 19, 2005 Response to Non-Final Office Action.

(56) References Cited

OTHER PUBLICATIONS

U.S. Appl. No. 09/746,670, Nov. 7, 2005 Notice of Allowance.
U.S. Appl. No. 09/746,670, Jan. 26, 2006 Request for Continued Examination.
U.S. Appl. No. 09/746,670, Oct. 2, 2006 Non-Final Office Action.
U.S. Appl. No. 09/746,670, Jan. 3, 2007 Response to Non-Final Office Action.
U.S. Appl. No. 09/746,670, Mar. 13, 2007 Final Office Action.
U.S. Appl. No. 09/746,670, May 14, 2007 Response to Final Office Action.
U.S. Appl. No. 09/746,670, Sep. 4, 2007 Notice of Allowance.
U.S. Appl. No. 10/600,257, Dec. 21, 2004 Non-Final Office Action.
U.S. Appl. No. 10/600,257, Mar. 24, 2005 Response to Non-Final Office Action.
U.S. Appl. No. 10/600,257, Jun. 7, 2005 Notice of Allowance.
U.S. Appl. No. 10/600,257, Sep. 9, 2005 Request for Continued Examination.
U.S. Appl. No. 10/600,257, Sep. 27, 2005 Non-Final Office Action.
U.S. Appl. No. 10/600,257, Nov. 28, 2005 Response to Non-Final Office Action.
U.S. Appl. No. 10/600,257, Jun. 4, 2008 Notice of Allowance.
U.S. Appl. No. 10/600,257, Apr. 17, 2009 Notice of Allowance.
U.S. Appl. No. 07/555,093, Oct. 22, 1991 Non-Final Office Action.
U.S. Appl. No. 07/555,093, Jan. 13, 1992 Response to Non-Final Office Action.
U.S. Appl. No. 07/555,093, Mar. 24, 1992 Notice of Allowance.
U.S. Appl. No. 08/103,087, Jan. 10, 1994 Non-Final Office Action.
U.S. Appl. No. 08/103,087, Jul. 28, 1994 Notice of Abandonment.
U.S. Appl. No. 09/775,775, Dec. 3, 2002 Notice of Allowance.
U.S. Appl. No. 08/273,329, Aug. 23, 1995 Non-Final Office Action.
U.S. Appl. No. 08/273,329, Dec. 26, 1995 Response to Non-Final Office Action.
U.S. Appl. No. 08/273,329, Apr. 8, 1996 Notice of Allowance.
U.S. Appl. No. 08/273,329, Jul. 2, 1996 Amendment after Notice of Allowance.
U.S. Appl. No. 08/273,329, Jul. 25, 1996 Response to Amendment.
U.S. Appl. No. 11/250,241, Jun. 12, 2009 Non-Final Office Action.
U.S. Appl. No. 07/385,290, Apr. 18, 1990 Non-Final Office Action.
U.S. Appl. No. 11/946,622, Jun. 3, 2009 Restriction Requirement.
U.S. Appl. No. 11/946,622, Jul. 30, 2009 Response to Restriction Requirement.
U.S. Appl. No. 11/946,622, Nov. 30, 2009 Non-Final Office Action.
U.S. Appl. No. 11/946,622, Feb. 23, 2010 Response to Non-Final Office Action.
U.S. Appl. No. 11/946,622, Mar. 1, 2011 Final Office Action.
U.S. Appl. No. 11/946,622, May 4, 2011 Response to Final Office Action.
U.S. Appl. No. 11/946,622, Jul. 21, 2011 Advisory Action.
U.S. Appl. No. 11/946,622, Aug. 8, 2011 Response to Final Office Action.
U.S. Appl. No. 11/946,622, Aug. 18, 2011 Advisory Action.
U.S. Appl. No. 11/946,622, Oct. 5, 2011 Response to Final Office Action.
U.S. Appl. No. 11/946,622, Oct. 7, 2011 Notice of Appeal.
Mar. 8, 2000 Food and Drug Administration 510(k) Premarket Notification letter.
"Parfums, Cosmetiques, Aromes: Japan approves sale of new cosmetics ingredient," Chemical Business Newsbase, Jan. 16, 2001.
(2000) "A-Z of exhibitors; at Central European Coatings Show." PPCJ. Polymers Paint Colour Journal, No. 4433, vol. 190: 42.
"Fraicheur de Peau Fresh Skin Body Mist," International Product Alert, No. 9, vol. 14, May 5, 1997.
"Happi, Household & Personal Products Industry: New ingredients galore at SCC supplier's day," Chemical Business Newsbase, Aug. 1, 2000.
"Manufacturing Chemist: Japan approve Schülke & Mayr's Sensiva SC 50," Chemical Business Newsbase, Jul. 14, 2000.
"S &M in Japan—Schülke & Mayr's Sensiva SC 50 deodorant active ingredient received approval for use in the Japanese market," SPC Asia No. 21, p. 35, May 2000.

"Schwarzkopf cares," European Cosmetic Markets, No. 5, vol. 13, May 1, 1996.
"Schwarzkopf: Moving into a new area," European Cosmetic Markets, No. 9, Sep. 1, 1996.
"Specific, Soap Perfumery and Cosmetics: New for deodorants: Sensiva SC 50," Chemical Business Newsbase, Aug. 12, 1999.
"Vichy launches oil-free moisturizer," Chemist & Druggist, p. 792, Jun. 8, 1996.
U.S. Appl. No. 11/946,622, Nov. 18, 2011 Notice of Allowance.
Baker. (1987) "In Controlled Release of Biologically Active Agents", John Wiley and Sons, pp. 156-162. (Table of Contents).
Baker, in Controlled Release of Biologically Active Agents, John Wiley & Sons, 1987, pp. 175-177.
Beilfuss. (1998) "A multifunctional ingredient for deodorants." SOFW Journal, 1998, vol. 124: 360, 362-364, 366.
Bleasel, N. et al. (2002) "Allergic contact dermatitis following exposure to essential oils." Australian Journal of Dermatology. 43: 211-213.
Brehm-Stecher, et al. (2003) "Sensitization of *Staphylococcus aureus* and *Escherichia coli* to Antibiotics by the Sesquiterpenoids Nerolidol, Farnesol, Bisabolol, and Apritone." Antimicrob Agents and Chemotherapy vol. 47: 3357-3360.
Gaonkar, et al. (2003) "Comparison of microbial adherence to antiseptic and antibiotic central venous catheters using a novel agar subcutaneous infection model." J Antimicrobial Chemotherapy 52: 389-396.
Greenfield, et al. (1995) "Decreased bacterial adherence and biofilm formation on chlorhexidine and silver sulfadiazine-impregnated central venous catheters implanted in swine." Crit Care Med. 23(5): 894-900.
Kupferwasser, et al. (2003) "Salicylic acid attenuates virulence in endovascular infections by targeting global regulatory pathways in *Staphylococcus aureus*." J Clin Invest. 112(2): 222-233.
Kupferwasser, et al. (1999) "Acetylsalicylic Acid Reduces Vegetation Bacterial Density, Hematogenous Bacterial Dissemination, and Frequency of Embolic Events in Experimental *Staphylococcus aureus* Endocarditis Through Antiplatelet and Antibacterial Effects" Circulation, 99: 2791-2797.
Modak et al. (2005) "A Topical Cream Containing a Zinc Gel (Allergy Guard) as a Prophylactic against Latex Glove-Related Contact Dematitis" Dermatitis, vol. 16 pp. 1-16.
Modak, S. M. et al. (1997) "A Topical Zinc Gluconate Gel Composition for the Prevention of latex/Starch Glove Related Allergic Reactions: Pilot Study in Volunteers." Programs and Abstracts of the 37th Interscience Conference on Antimicrobial Agents and Chemotherapy, Toronto: American Society for Microbiology Washington DC. Abstract J-52.
Pacheo,-Fowler et al. (2004) "Antiseptic impregnated endotracheal tubes for the prevention of bacterial colonization." J Hospital Infection 57: 170-174.
Robinson K "Heat beating technology; deodorant market," Soap Perfumery and Cosmetics, v. 69 No. 7 p. 34, Jul. 1996.
Sampath, et al. (1995) "Infection resistsance of surface modified catheters with either short-lived or prolonged activity" Journal of Hospital Infection vol. 30, 201-210.
Sampath, et al. (2001) "In vitro and in vivo efficacy of catheters impregnated with antiseptics or antibiotics: evaluation of the risk of bacterial resistance to the antimicrobials in the catheters." Infection Control and Hospital Epidemiology 22(10): 640-646.
Sampath, et al. (2001) "Safety and efficacy of an improved antiseptic catheter impregnated intraluminally with chlorhexidine." J of Infusion Nursing 24(6): 395-403.
Sensiva® SC 50 product description from manufacturer website (www.schuelke-mayr.com), Schülke & Mayr, manufacturer, printed Apr. 4, 2001.
Woodruff, J "Mixed feelings," Soap Perfumery & Cosmetics, No. 9, vol. 73, p. 39, Sep. 1, 2000.
Raad, I. "Intravascular-catheter-related infections," *The Lancet*, 351:893-898 (1998).
Addy et al., "In vitro studies into the relaes of chlorhexidine acetate, predisolone sodium phosphate, and prednisolone alcohol from cold cure denture base acrylic", *Journal of Biomedical Materials Research*, 16:145-157 (1982).

(56) References Cited

OTHER PUBLICATIONS

Brook et al., "Controlling drug release from acrylic polymers: In Vitro studies with potential oral inserts", *Biomaterials*, 7:292-296 (1986).
Coventry et al., "Experimental use of a slow release device employing chlorhexidine gluconate in areas of acute periodontal inflamation", *J. of Clinical Periodontology*, 9:129-133 (1982).
Harper et al., "Simple additives to increase the activity of chlorhexidine digluconate against urinary pathogens", *Paraplegia*, 21:86-93 (1983).
Inman et al., "Prospective comparison of silver sulfadiazine 1 percent plus chlorhexidine digluconate 0.2 percent (Slivazine) and silver sulfadiazine 1 percent (Flazine) as prophylaxis against burn wound infection", *Burns*, 11:35-40 (1984).
Messing et al., "Antibiotic-Lock Technique is an Effective Treatment of Bacterial Catheter-Related Sepsis During Parenteral Nutrition", *Clinical Nutrition*, 9:220-225 (1990).
Mitchell et al., "Instrumental Bacteraemia and its prevention", *British Journal of Urology*, 34:454-458 (1962).
Nakano et al., "Efficacy of a latex foley catheter with sustained release of chlorohexidine: 1st Report, clinical Trails for Prevention of Urinary Tract Infection", *Hinyokika Kiyo*, 32(4):567-574 (1986).
Quesnel et al., "Synergism between chlorhexidine and sulphadiazine", *Appl. Bact.*, 45:397-405 (1978).
Paterson et al., "Urinary infection after colporrhapy: its incidence, causation and prevention", *Journal of Obstetrics and Gynecology*, 67:394-401 (1960).
Segura et al., "In Vitro Bacteriological Study of a New Hub Model for Intravascular Catheters and Infusion Equipment", *Journal of Clinical Microbiology*, 27(12):2656-2659 (1989).
Snelling et al., "Comparison of 1 percent silver sulfadiazine with and without 1 percent chlorhexidine digluconate for topical antibacterial effect in the burnt infected rat", *J. Burn Cap and Rehab*, 9(1):35-40 (1988).
Tuominen et al., "The effect of local antiseptic, chlorhexidine, in preventing infection from central venous catherization", *Abnnals of Clinical Research*, 13:425-428 (1981).
Haung et al., "Reduction of polysaccharide production in *Pseudomonas aeruginosa* biofilms by bismuth dimercaprol (BisBAL) treatment", *J. antimicorb. Chemother.*, 44:601-605 (1999).
Domenico et al., "Enhancement of bismuth antibacterial activity with lipophilic thiol chelators", *Antimicrob Ag Chemother*, 41:1697-1703 (1997).
Domenico et al., "Bismuth-dimercaprol exposes surface components of *Klebsiella pneumoniae* camouflaged by the polysaccharide capsule", *Ann. NY Acad. Sci.*, 797:269-270 (1996).
Sheretz et al., "Efficacy of antibiotic-coated catheters in preventing subcutaneous *Staphylococcus aureus* infection in rabbits", *J. Infect. Dis.*, 167:98-106 (1993).
Domenico et al., "Reduction of capsular polysaccharide and potentiation of aminoglycoside inhibition in gram-negative bacteria by bismuth subsalicylate", *J. Antimicrob.*, 28:801-810 (1991).
Bierer, "Bismuth subsalicylate: history, chemistry, and safety", Rev. Inf. Dis., 12 Suppl 1:S3-S8 (1990).
Leon-Barau et al., "In vitro and in vivo effects of three bismuth compounds in fermentation by colonic bacteria", Rev. Inf. Dis., 12 Suppl 1:S24-S29 (1990).
Goodmand and Gillman's, The Pharmacological Basis of Therapeutics, Gilman et al., editors, Seventh Edition, 1985, Macmillan Publishing Company, New York, pp. 959-960, 1066-1067, 1171.
The Merck Index, Ninth Edition, 1976, p. 1187.
The Merck Index, An Encyclopedia of Chemicals, Drugs and Biologicals, Tenth Edition. Merck & Co., Inc., Rahway, NJ, 1983, p. 1092.
Lelah and Cooper, 1986, Polyurethanes in Medicine, CRC Press, Inc., FL., pp. 57-67.
Bach et al., 1994 "Prevention of bacterial colonization of intravenous catheters by antiseptic impregnation polymers," J. Antimicrobial Chemotherapy 33: 969-978.
Choi L, Choudhri AF, Pillarisetty VG, Sampath LA, Caraos L, Brunnert SR, Oz MC, Modak SM. Development of an infection-resistant LVAD driveline: a novel approach to the prevention of device-related infections. J. Heart Lung Transplant. Nov. 1999;18 (11):1103-10.
On Apr. 17, 2000, which is prior to the Dec. 22, 2000 filing date of the present application (U.S. Appl. No. 09/746,670), a triple lumen catheter was sold by the licensee, Arrow Incorporated, in the United States. This catheter had an outer coating prepared using a solution containing three percent (3%) weight by volume (w/v) of chlorhexidine diacetate and 0.75 percent w/v silver sulfadiazine. The catheter had an inner lumen coating prepared using a solution containing the solvent ethanol, 0.75 percent (0.75%) w/v chlorhexidine free base, and 0.75 percent (0.75%) w/v chlorhexidine diacetate.
Tambe SM, Sampath L, Modak SM. In vitro evaluation of the risk of developing bacterial resistance to antiseptics and antibiotics used in medical devices. J. Antimicrob. Chemother. May 2001;47 (5):589-98.
Kim CY, Kumar A, Sampath L, Sokol K, Modak S. Evaluation of an antimicrobial-impregnated continuous ambulatory peritoneal dialysis catheter for infection control in rats. Am. J. Kidney Dis. Jan. 2002;39 (1):165-73.
Gaonkar TA, Sampath LA, Modak SM. Evaluation of the antimicrobial efficacy of urinary catheters impregnated with antiseptics in an in vitro urinary tract model. Infect Control Hosp Epidemiol. Jul. 2003;24 (7):506-13.

\* cited by examiner

ANTIMICROBIAL MEDICAL DEVICES CONTAINING CHLORHEXIDINE FREE BASE AND SALT

CROSS-REFERENCE TO RELATED APPLICATIONS

This application is a continuation of U.S. patent application Ser. No. 11/946,622, filed Nov. 28, 2007, which is a divisional of U.S. patent application Ser. No. 09/746,670, filed Dec. 22, 2000, which issued as U.S. Pat. No. 7,329,412, the contents of each of which are incorporated herein by reference in their entireties, and to each of which priority is claimed.

INTRODUCTION

The present invention relates to medical devices treated with a solution comprising a combination of chlorhexidine free base and a water-soluble chlorhexidine salt, in a ratio that facilitates chlorhexidine uptake by the devices and hence improves antimicrobial effectiveness.

BACKGROUND OF THE INVENTION

Whenever a medical device comes in contact with a patient, a risk of infection is created. Thus, a contaminated examination glove, tongue depressor, or stethoscope could transmit infection. The risk of infection dramatically increases for invasive medical devices, such as intravenous catheters, arterial grafts, intrathecal or intracerebral shunts and prosthetic devices, which not only are, themselves, in intimate contact with body tissues and fluids, but also create a portal of entry for pathogens.

Catheter related infections, especially blood stream infections, are associated with increased morbidity (10 to 20 percent), prolonged hospitalization (by a period having a mean of seven days), and increased medical costs (approximately $6,000 per hospitalization). According to a survey of intensive care units from 1986 through 1990 by the National Nosocomial Infection Surveillance System, the rate of catheter-related blood stream infections ranged from 2.1 to 30.2 per 1,000 catheter-days. Infections associated with central venous catheters have been reported to result from the transcutaneous migration of the pathogens from the insertion site with the eventual colonization of the catheter tip. In addition, intraluminal colonization has been suggested to result from contaminated hubs and infusates that contribute to catheter related blood stream infections. The longer the duration of catheterization, the greater the susceptibility to either luminal or outer surface colonization of catheters. Even for short term use of catheters, infections have been reported due to contamination of the insertion sites.

A number of methods for reducing the risk of infection have been developed which incorporate anti-infective agents into medical devices. Such devices desirably provide effective levels of anti-infective agent during the period that the device is being used. Sustained release may be problematic to achieve, in that a mechanism for dispensing anti-infective agent over a prolonged period of time may be required, and the incorporation of sufficient amounts of anti-infective agent may adversely affect the surface characteristics of the device. The difficulties encountered in providing effective antimicrobial protection increase with the development of drug-resistant pathogens.

One potential solution to these problems is the use of a synergistic combination of anti-infective agents that requires relatively low concentrations of individual anti-infective agents which may have differing patterns of bioavailability. For example, WO 97/25085 relates to medical devices comprising synergistic combinations of chlorhexidine and triclosan. U.S. Pat. Nos. 5,616,338 and 5,019,096 relate to infection resistant medical devices comprising synergistic combinations of a silver salt, a biguanide (such as chlorhexidine) and a polymeric component that forms a matrix to provide a sustained release of the silver salt and biguanide.

U.S. Pat. Nos. 5,165,952 and 5,451,424 relate to medical articles with chlorhexidine both coated on and bulk distributed throughout the medical articles. When chlorhexidine is bulk distributed it adversely affects certain characteristics of the device such as tensile strength, and the high temperatures needed for extension of plastics such as polyurethane may damage the chlorhexidine.

U.S. Pat. No. 5,089,205 relates to incorporation of chlorhexidine free base or one of its salts in a medical device such as a glove by both a distribution or dipping process.

Chlorhexidine is a broad spectrum antimicrobial agent and has been used as an antiseptic for several decades with minimal risk of developing resistant microbes. When relatively soluble chlorhexidine salts, such as chlorhexidine acetate, were used to impregnate catheters, the release was undesirably rapid. The duration of the antimicrobial efficacy of medical devices impregnated with chlorhexidine salts, such as chlorhexidine acetate, is short lived. Chlorhexidine free base is not soluble in water or alcohol and cannot be impregnated in sufficient amounts because of low solubility in a solvent system.

In contrast to the present invention, none of the above-cited references teach medical articles treated with a solution comprising a combination of chlorhexidine free base and a water-soluble chlorhexidine salt, at particular ratios, which provide improved antimicrobial effectiveness through an increased uptake of chlorhexidine into the medical device, increased retention of chlorhexidine in the medical device and prolonged release of chlorhexidine from the medical device, while utilizing relatively low levels of chlorhexidine,

SUMMARY OF THE INVENTION

The present invention relates to medical devices treated with a solution comprising one or more solvents and a combination of chlorhexidine free base and a water-soluble chlorhexidine salt, in a weight/weight ratio of between about 1:1 to about 1:5 (inclusive), preferably about 1:1 of chlorhexidine free base to chlorhexidine salt. The invention further relates to methods of preparing medical devices by exposing them, in whole or in part, to a solution comprising one or more solvents and the above-recited combinations of chlorhexidine free base and chlorhexidine salt.

This invention is based, at least in part, on the discovery that devices treated with combinations of chlorhexidine free base and a water-soluble chlorhexidine salt exhibit improved antimicrobial effectiveness due to increased uptake of chlorhexidine into the medical device, increased retention of chlorhexidine in the medical device, and prolonged release of chlorhexidine while utilizing relatively low levels of chlorhexidine, and, in certain non-limiting embodiments, in the absence of agents other than chlorhexidine. In particular, while it had been previously found that triclosan can be particularly useful when used in conjunction with chlorhexidine free base, it has been further discovered that medical articles having suitable antimicrobial properties may be prepared, according to the present invention, without the use of triclosan. Therefore, in particular embodiments, medical articles according to the present invention offer the advantage of preventing or inhibiting infection while avoiding undesirable adverse reactions to antimicrobial agents other than chlorhexidine by allergic individuals.

DETAILED DESCRIPTION OF THE INVENTION

The present invention provides for medical articles treated with a solution comprising one or more solvents and a combination of chlorhexidine free base ("CHX") and a water-soluble chlorhexidine salt, and further provides for methods of preparing medical devices by exposing the device, in whole or in part, to said solution.

While not being bound or limited by any particular theory, it is believed that the combination of CHX and water-soluble chlorhexidine salt forms a soluble complex. This would explain the increased uptake of chlorhexidine into the medical device, increased retention of chlorhexidine in the medical device, and increased sustained release of chlorhexidine from the medical device while utilizing relatively low levels of chlorhexidine in the absence of agents other than chlorhexidine.

The following are definitions of terms used herein unless otherwise indicated:

Water soluble chlorhexidine salts have a solubility of at least about 2.0 grams per 100 ml in water at 20° C. Examples of water soluble chlorhexidine salts include chlorhexidine diacetate (also referred to herein as chlorhexidine acetate, or "CHA") and chlorhexidine digluconate (or "CHG") with CHA being preferred.

The terms "medical article" and "medical device" are used interchangeably herein. Medical articles that may be treated according to the invention are either fabricated from and/or coated or treated with biomedical polymer (and hence may be referred to as "polymeric medical articles") and include, but are not limited to, catheters including urinary catheters and vascular catheters (e.g., peripheral and central vascular catheters), wound drainage tubes, arterial grafts, soft tissue patches (such as polytetrafluoroethylene (PTFE) soft tissue patches), gloves, condoms, shunts, stents, tracheal catheters, wound dressings, sutures, guide wires and prosthetic devices (e.g., heart valves and LVADs). Vascular catheters which may be prepared according to the present invention include, but are not limited to, single and multiple lumen central venous catheters, peripherally inserted central venous catheters, emergency infusion catheters, percutaneous sheath introducer systems and thermodilution catheters, including the hubs and ports of such vascular catheters. The present invention may be further applied to medical articles that have been prepared according to U.S. Pat. Nos. 5,616,338 and 5,019,096 by Fox, Jr. et al. and U.S. Pat. No. 5,772,640 by Modak et al.

The term "hydrophilic polymeric medical article" is a medical article fabricated from a hydrophilic polymer. As used herein, "hydrophilic polymer" refers to polymers that have a water absorption greater than 0.6 percent by weight (and, in preferred embodiments, less than 2 percent by weight; as measured by a 24 hour immersion in distilled water, as described in ASTM Designation D570-81) including, but not limited to biomedical polyurethanes (e.g., ether-based polyurethanes and ester-based polyurethanes, as set forth in Faker, 1987, in *Controlled Release of Biologically Active Agents*, John Wiley and Sons, pp. 175-177 and Lelah and Cooper, 1986, *Polyurethanes in Medicine*, CRC Press, Inc., Fla. pp. 57-67; polyurethanes comprising substantially aliphatic backbones such as Tecoflex™ 93A; polyurethanes comprising substantially aromatic backbones such as Tecothane™; and Pellethane™), polylactic acid, polyglycolic acid, natural rubber latex, and gauze or water-absorbent fabric, including cotton gauze and silk suture material.

The term "hydrophobic polymeric medical article" is a medical article fabricated from a hydrophobic polymer. As used herein, "hydrophobic polymer" refers to a polymer that has a water absorption of less than 0.6% (w/w) and includes, but is not limited to, silicone polymers such as biomedical silicones (e.g., Silastic Type A) or elastomers (e.g., as set forth in Baker, 1987, in *Controlled Release of Biologically Active Agents*, John Wiley and Sons, pp. 156-162), Dacron, PTFE (also "Teflon"), expanded PTFE, polyvinyl chloride (PVC), cellulose acetate, polycarbonate, and copolymers such as silicone-polyurethane copolymers (e.g., PTUE 203 and PTUE 205 polyurethane-silicone interpenetrating polymer).

The terms "treat", "treated", "treating", etc., as used herein, refer to coating, impregnating, or coating and impregnating a medical article with anti-infective agent. Medical articles are "treated" by exposing them, for an effective period of time, to a treatment solution, where an "effective period of time" is that period of time sufficient to introduce anti-infective qualities of the anti-infective agent to the articles. Medical articles may be dipped, soaked, or otherwise have a surface coated. The term "dipped" suggests briefer exposure to the treatment solution relative to "soaking," and preferably is for a period of time less than fifteen minutes.

Percentages recited herein refer to weight/volume (w/v), except as indicated otherwise (e.g., volume/volume or "v/v").

The term "CFU" means colony forming unit.

The term "about" indicates a variation within 20 percent.

The present invention provides for medical articles treated with a solution comprising one or more solvents and a combination of CHX and a water-soluble chlorhexidine salt, in a weight/weight ratio of between about 1:1 and 1:5, preferably about 1:1. Such medical articles include hydrophilic polymeric medical articles as well as hydrophobic polymeric medical articles fabricated from and/or coated or treated with such a biomedical polymer. In addition, the present invention may be applied to medical articles that have been prepared according to U.S. Pat. Nos. 5,616,338 and 5,019,096 by Fox, Jr. et al. and U.S. Pat. No. 5,772,640 by Modak et al. Such one or more solvents may be selected from the group consisting of water, reagent alcohol, and tetrahydrofuran ("THF"), dimethylsulfoxide, dimethylformamide, N-methyl-2-pyrrolidone, and mixtures thereof.

In a specific non-limiting embodiment, the treatment solution comprises CHX-CHA in a weight/weight ratio between about 1:1 and about 1:5, preferably about 1:1 of CHX to CHA.

The present invention further provides, in a non-limiting embodiment, for methods of preparing medical devices by treating the device, in whole or in part, with a solution comprising one or more solvents and a complex formed by synergistic combinations of chlorhexidine free base and chlorhexidine acetate.

In non-limiting embodiments, medical articles may be treated with a solution comprising the steps of (i) placing the medical article in a solution comprising (a) a solvent selected from the group consisting of water, reagent alcohol, THF, dimethylsulfoxide, dimethylformamide, N-methyl-2-pyrrolidone, and mixtures thereof and (b) a mixture of CHX and a water-soluble chlorhexidine salt, preferably CHA, preferably in a weight/weight ratio of between about 1:1 and about 1:5; (ii) soaking the medical article in the solution for an effective period of time to allow the medical article to swell and to incorporate the anti-infective agents; (iii) removing the medical article from the solution; and (iv) drying the medical article.

Medical articles prepared according to the invention may be treated on an external surface, internal surface, or both. For example, and not by way of limitation, where the medical article is a catheter having a lumen, the internal (i.e., luminal) surface and/or external surface of the catheter may be treated together or separately according to the invention. An open-ended catheter may be placed in a treatment solution such that the internal and external surfaces are exposed to the treatment solution. Alternatively, the ends of the catheter may be sealed before being placed in the treatment solution so that only the external surface is exposed to the treatment solution. Alternatively, only the internal surface may be exposed to the treatment solution if the solution is pushed, pulled or allowed to pass through and/or fill the lumen without immersing the catheter in the treatment solution.

In specific non-limiting embodiments, a catheter having a lumen may be treated with a solution comprising the steps of (i) exposing the lumen of the catheter to a solution comprising (a) a solvent selected from the group consisting of water, alcohol, THF, dimethylsulfoxide, dimethylformamide, N-methyl-2-pyrrolidone, and mixtures thereof and (b) a mixture of CHX and a water-soluble chlorhexidine salt, preferably CHA, preferably in a molar ratio of between about 1:1 and about 1:5; (ii) filling the lumen of the catheter with the solution by pushing, pulling, or allowing passage of the solution into the lumen for an effective period of time to allow the material surrounding the lumen of the catheter to swell and to incorporate the chlorhexidine; (iii) removing the solution from the lumen of the catheter; and (iv) drying the catheter.

In the foregoing methods, the duration of exposure of the medical article or portion thereof to the treatment solution may preferably, but not by limitation, be ten seconds to one hour. The duration of exposure of the lumen of a catheter may preferably, but not by limitation, be ten seconds to two minutes. Longer periods of exposure may be used provided that undesirable deterioration of the medical article does not occur.

The treatment solutions may optionally further comprise (i) an organic acid, at a concentration of between about 0.1 and about 5 percent, preferably between about 0.1 and about 2 percent; (ii) an anti-inflammatory agent, at a concentration of between about 0.1 and about 5 percent, preferably between about 0.1 and about 1 percent; and/or (iii) a hydrogel at a concentration of between about 0.5 to about 10 percent, preferably between about 1 and about 5 percent.

WORKING EXAMPLES

The following methods were used in performing experiments discussed in the following examples, unless indicated otherwise:

Method of Treatment of a Medical Article with Solution.

The medical article was treated by exposing the entire medical article, or a portion thereof, to a solution containing CHA alone, CHX alone or the CHX-CHA combination in various amounts in a solvent system. The medical article, or a portion thereof, was exposed by soaking the article in the solution for 100 seconds before removing the article from the solution. For articles, such as catheters, having an internal lumen, the solution was pushed into the lumen and allowed to remain for 100 seconds before removal.

Method of Determining Drug Uptake.

The amount of drug uptake into the treated polymeric medical articles was determined using a spectrophotometric method after extraction in alcohol.

Method of Determining Long Term Antimicrobial Efficacy in Catheter Lumen.

In order to determine the duration of antimicrobial efficacy in catheter lumens exposed to treatment solutions, catheters were perfused for 7 days using the following continuous perfusion model. The distal lumens of catheters were connected to a peristaltic pump in a closed loop, wherein 1.5 L of 10% (v/v) trypticase soy broth in saline was constantly perfused by recycling it through each catheter lumen at a rate of 83 ml/hr for 7 days. On the eighth day the catheters were disconnected and used for evaluation of bacterial adherence.

Method of Evaluating Microbial Adherence to a Catheter Lumen.

After perfusion of catheters for 7 days as set forth above, the distal lumens of each catheter were filled with a $10^8$ CFU/ml culture of bacteria or yeast. In the case of exposure to *E. aerogenes*, *P. aeruginosa* and *C. albicans*, cultures containing $10^6$ CFU/ml were used. The ends of the catheters were heat sealed and the catheters were incubated for 24 hours in an orbital shaker at 37° C. After 24 hours, the lock cultures were collected from the lumen and subcultured after serial dilution using agent inactivating media. The outer surface of the whole catheter was sterilized by wiping the outer surface with an alcohol swab. Thereafter, the lumens were flushed with 20 ml trypticase soy broth to remove non-adherent bacteria. The body of the catheters were subdivided into 2 cm segments, which were further cut into 2 mm subsegments. The subsegments were placed in 4.0 ml agent inactivating media and sonicated in a 4° C. water bath using an Astrasan Sonicator (Model 9T) at 60 KHertz. Thereafter, 0.5 ml of the extract was then subcultured on a trypticase soy agar plate and incubated at 37° C. for 24 hours. Colony counts were then determined.

Method of Evaluating Bacterial Adherence to PTFE Soft Tissue Patch Disks.

Polytetrafluoroethylene (PTFE) disks were soaked and agitated in 3.0 ml of media containing 50% (v/v) bovine adult serum and 50% (v/v) trypticase soy broth. The media was changed on days 1, 2 and 4. On the fourth day, $10^5$ CFU/ml of bacteria was added to the media. On the fifth clay, the disks were removed, rinsed and rolled on drug inactivating agar. The plates were then incubated for 24 hours at 37° C. Colony counts were determined thereafter.

Method of Determining Zones of Inhibition.

Zones of inhibition were measured by seeding a specified amount of bacteria onto a trypticase soy agar plate. Then, three units of a specified amount of medical article were placed on the plate. The plates were incubated at 37° C. for 24 hours. The zones of inhibition were then measured for Day 1. To measure the zones of inhibition on Day 2 and subsequent days, the units of medical article were transferred onto a fresh plate of similarly prepared agar, incubated at 37° C. for 24 hours and colony-free zones were measured.

Example

Polyurethane Central Venous Catheters

Polyurethane central venous catheters, which are hydrophilic polymeric medical articles, were separated into three otherwise identical groups of catheters and separately treated with a solution that either (i) contained no antimicrobial agents; (ii) contained CHA alone, or (iii) contained a combination of CHX and CHA ("CHX-CHA") in accordance with the present invention. In particular, the luminal surfaces of the catheters were separately treated with one of the following solutions:

(1) a solvent system of 80% (v/v) reagent alcohol and 20% (v/v) THF with no antimicrobial agents;

(2) 2.4% CHA in a solvent system of 80% (v/v) reagent alcohol and 20% (v/v) THF; and (3) 1.2% CHX and 1.2% CHA in a solvent system of 80% (v/v) reagent alcohol and 20% (v/v) THF.

The solution was exposed to the luminal surface of the catheter by pushing the solution into the lumen and allowing the solution to remain in the lumen for 100 seconds. Thereafter, the solution was removed, and the distal lumens of the catheters were connected to a peristaltic pump in a closed loop, wherein 1.5 L of 10% trypticase soy broth in saline was constantly perfused by recycling it through each catheter lumen at a rate of 83 ml/hr for 7 days, according to the continuous perfusion method discussed above. On the eighth day the catheters were disconnected and the ability of bacteria to adhere to the lumens was tested as follows.

The distal lumens of each of the three groups of catheters were separately filled with $8 \times 10^8$ CFU/ml culture of *S. epidermidis*. The ends of the catheters were heat sealed and the catheters were incubated for 24 hours in an orbital shaker at 37° C. After 24 hours, the lock cultures were collected from the lumen and subcultured after serial dilution using agent inactivating media. The outer surface of the whole catheter was sterilized by wiping the outer surface with an alcohol swab. Thereafter, the lumens were flushed with 20 ml trypticase soy broth to remove non-adherent bacteria. The bodies of the catheters were subdivided into 2 cm segments, which were further cut into 2 mm subsegments. The subsegments were placed in 4.0 ml agent inactivating media and sonicated in a 4° C. water bath using an Astrasan Sonicator (Model 9T) at 60 KHertz. Thereafter, 0.5 ml of the extract was then subcultured on a trypticase soy agar plate and incubated at 37° C. for 24 hours. Colony counts were then determined and are shown below in Table 1.

The luminal surfaces of catheters were also tested according to the above described techniques to evaluate the adherence of a wide variety of organisms. The luminal surfaces of catheters were separately treated with the following solutions:

(1) a solvent system of 80% (v/v) reagent alcohol and 20% (v/v) THF with no antimicrobial agents; and (2) 1.2% CHX and 1.2% CHA in a solvent system of 80% (v/v) reagent alcohol and 20% (v/v) THF.

The luminal surfaces were exposed to the respective solutions for 100 seconds. Thereafter, the solutions were removed, and the lumens were perfused according to the continuous perfusion method discussed above.

On the eighth day, the catheters were disconnected and susceptibility to microbial adherence was evaluated. The distal lumens of each group of catheters were separately filled with the following amounts of bacteria (*S. aureus*, *P. aeruginosa*, and *Enterobacter*) or yeast (*C. albicans*):

(1) $8 \times 10^8$ CFU/ml culture of *S. aureus*;

(2) $8 \times 10^6$ CFU/ml culture of *P. aeruginosa*;

(3) $8 \times 10^8$ CFU/ml culture of *Enterobacter*; and (4) $8 \times 10^6$ CFU/ml culture of *C. albicans*.

The four subgroups of lumens were prepared for evaluating microbial adherence to the catheter lumens as described above. The ends of the catheters were heat sealed, incubated, subcultured, externally sterilized, flushed, subdivided, placed in inactivating media and sonicated according to the techniques set forth supra. Thereafter, 0.5 ml of the extract was subcultured, incubated and examined to determine the colony counts. The results are shown below in Table 2.

TABLE 2

| Solution | Adherence of *S. aureus* (CFU/cm) | Adherence of *P. aeruginosa* (CFU/cm) | Adherence of *Enterobacter* (CFU/cm) | Adherence of *C. albicans* (CFU/cm) |
|---|---|---|---|---|
| 80% (v/v) reagent alcohol + 20% (v/v) THF | $1.3 \times 10^4$ | $>10^5$ | $>10^5$ | $1.7 \times 10^4$ |
| 1.2% CHX + 1.2% CHA in 80% (v/v) reagent alcohol + 20% (v/v) THF | 3 | 9 | 2 | 26 |

TABLE 1

| Solution | Bacterial Adherence of *S. epidermidis* (CFU/cm) |
|---|---|
| 80% (v/v) reagent alcohol + 20% (v/v) THF | $2.2 \times 10^4$ |
| 2.4% CHA in 80% (v/v) reagent alcohol + 20% (v/v) THF | $3 \times 10^2$ |
| 1.2% CHX + 1.2% CHA in 80% (v/v) reagent alcohol + 20% (v/v) THF | 2 |

The results shown in Table 1 demonstrate the synergistic antimicrobial effect of treating a polyurethane central venous catheter lumen with a solution comprising the mixture of CHX and CHA. Table 2 shows that articles treated with CHX and CHA exhibit an increased effectiveness across a wide variety of organisms by decreasing luminal adherence substantially more than articles treated with no antimicrobial agents.

In a further study, the luminal surface of three groups of otherwise identical polyurethane central venous catheters were separately treated with one of the following three solutions:

(1) 2% CHA in a solvent system of 80% (v/v) ethanol and 20% (v/v) THF;

(2) 0.625% CHX and 1.375% CHA in a solvent system of 80% (v/v) ethanol plus 20% (v/v) THF; and (3) 1% CHX and 1% CHA in a solvent system of 80% (v/v) ethanol plus 20% (v/v) THF.

The solution was pushed into the lumen and allowed to remain for 100 seconds.

The amount of uptake of chlorhexidine in the catheters was determined using a spectrophotometric method after extraction with alcohol.

In order to determine the amount of drug retention and antimicrobial efficacy, the catheters were perfused for 6 days with 1.500 L of saline per day. The treated catheters were then studied on Day 1 and Day 6 after perfusion to determine the amount of drug retention. The chlorhexidine in the catheter after perfusion was determined using a spectrophotometric method after extraction with alcohol. The antibacterial activity was measured on Day 6 after perfusion by counting the CFU/cm of *S. epidermidis*. Table 3 shows results of the uptake, drug retention and antibacterial activity of the treated catheters.

TABLE 3

| Solution | Uptake (µg/cm) | Retention of Drug (µg/cm) Day 1 | Day 6 | Antibacterial Activity (CFU/cm) *S. epidermidis* Day 6 |
|---|---|---|---|---|
| 2% CHA in 80% (v/v) Ethanol + 20% (v/v) THF | 44 | 34 | 8 | $10^2$ |
| 0.625% CHX + 1.375% CHA in 80% (v/v) Ethanol + 20% (v/v) THF | 70 | 43 | 22 | 0 |
| 1% CHX + 1% CHA in 80% (v/v) Ethanol + 20% (v/v) THF | 80 | 45 | 26 | 0 |

These results demonstrate the synergistic antimicrobial effect of treating a polyurethane central venous catheter lumen with a solution comprising a mixture of CHX and CHA.

Example

Urinary Catheters

Hydrophilic urinary catheters were separated into two otherwise identical groups, and the whole catheters (i.e., external and luminal surfaces of the catheter) were treated with a solution containing either:

(1) 4% CHA in a solvent system of 85% (v/v) THF and 15% (v/v) methanol; or (2) 2% CHX plus 2% CHA in a solvent system of 85% (v/v) THF and 15% (v/v) methanol.

The catheters of each group were soaked in the respective solution for 30 minutes to one hour. Thereafter, the catheters were removed from the solution.

The amount of uptake of chlorhexidine was determined using a spectrophotometric method after extraction with alcohol, which results are shown below in Table 4.

The two groups of catheters were separately exposed to cultures of *P. aeruginosa* and *C. albicans* in order to study the antimicrobial efficacy of the medical article. Trypticase soy agar plates were seeded with 0.3 ml of $10^8$ CFU/ml of *P. aeruginosa* and *C. albicans*, respectively. Thereafter, a 0.5 cm length of urinary catheter was placed on each plate with three units per plate. The plates were then incubated for 24 hours at 37° C. After 24 hours, the zones of inhibition were measured for Day 1. To measure the zones of inhibition for Day 2 to Day 6, the process was repeated upon transferring the units to fresh agar plates similarly prepared. The results are shown in Table 4.

TABLE 4

| Solution | Uptake (µg/cm) | Antimicrobial Efficacy (Zone of Inhibition (mm)) *P. aeruginosa* Day | | | | | | Antimicrobial Efficacy (Zone of Inhibition (mm)) *C. albicans* Day | | | | | |
|---|---|---|---|---|---|---|---|---|---|---|---|---|---|
| | | 1 | 2 | 3 | 4 | 5 | 6 | 1 | 2 | 3 | 4 | 5 | 6 |
| 4% CHA in 85% (v/v) THF + 15% (v/v) Methanol | 123 | 15 | 11 | 10 | 9 | 0 | 0 | 11 | 9 | 0 | 0 | 0 | 0 |
| 2% CHX + 2% CHA in 85% (v/v) THF + 15% (v/v) Methanol | 380 | 16 | 13 | 11 | 10 | 10 | 10 | 12 | 11 | 11 | 10 | 9 | 6 |

These results demonstrate the synergistic antimicrobial effect of treating the urinary catheters with a solution comprising a mixture of CHX and CHA.

Example

PTFE Soft Tissue Patches

Disks cut from PTFE soft tissue patches, which are hydrophobic polymeric medical articles, were treated with a solution that contained CHA alone and a solution that contained a CHX-CHA complex in accordance with the present invention. Groups of disks having a 1 mm thickness were treated for one hour with one of the following solutions:

(1) 0.4% CHA in a solvent system of 70% (v/v) THF and 30% (v/v) methanol; or (2) 0.2% CHX and 0.2% CHA in a solvent system of 70% (v/v) THF and 30% (v/v) methanol.

The amount of uptake of chlorhexidine in the PTFE disks was determined using a spectrophotometric method after extraction with alcohol, and the results are shown below in Table 5.

The two groups of disks were separately exposed to cultures of $P.\ aeruginosa$ and $S.\ epidermidis$ in order to study their antimicrobial efficacy. Trypticase soy agar plates were seeded with 0.3 nil of $10^8$ CFU/ml of $P.\ aeruginosa$ and $C.\ albicans$, respectively. Thereafter, 0.5 cm diameter disks were placed on each plate with three units per plate. The plates were then incubated for 24 hours at 37° C. After 24 hours, the zones of inhibition were measured for Day 1. The process was repeated upon transferring the disks to fresh agar plates similarly prepared for Day 2 to Day 6. The zones of inhibition are shown in Table 5.

TABLE 5

| Solution | Uptake (µg/cm) | Antimicrobial Efficacy (Zone of Inhibition (mm)) P. aeruginosa Day | | | | Antimicrobial Efficacy (Zone of Inhibition (mm)) S. epidermidis Day | | | |
|---|---|---|---|---|---|---|---|---|---|
| | | 1 | 2 | 3 | 4 | 1 | 2 | 3 | 4 |
| 0.4% CHA in 70% (v/v) THF + 30% (v/v) Methanol | 450 | 8 | 5 | 0 | 0 | 12 | 10 | 9 | 9 |
| 0.2% CHX + 0.2% CHA in 70% (v/v) THF + 30% (v/v) Methanol | 840 | 12 | 8 | 8 | 7 | 15 | 13 | 12 | 11 |

These results demonstrate the synergistic effect of treating PTFE soft tissue patches with a solution comprising a mixture of CHX and CHA.

Bacterial adherence on PTFE soft tissue patch disks treated with CHA alone, CHX alone, or a mixture of CHA and CHX were studied. 2 mm thick disks were separated into four groups and separately treated with one of the following solutions:

(1) a solvent system of 70% (v/v) THF and 30% (v/v) methanol with no antimicrobial;

(2) 0.4% CHA in a solvent system of 70% (v/v) THF and 30% (v/v) methanol;

(3) 0.4% CHX in a solvent system of 70% (v/v) THF and 30% (v/v) methanol; and (4) 0.2% CHX and 0.2% CHA in a solvent system of 70% (v/v) THF and 30% (v/v) methanol.

In order to determine the bacterial adherence to the PTFE, three disks of 1 cm diameter from patches in each treatment group were soaked and agitated in 3.0 ml of media containing 50% (v/v) bovine adult serum and 50% (v/v) trypticase soy broth. The media was changed on days 1, 2 and 4. On the fourth day, $10^5$ CFU/ml of $S.\ aureus$ was added to the media. On the fifth day after agitation in media, the disks were removed, rinsed and rolled on to plates of drug inactivation agar. The plates were then incubated for 24 hours at 37° C. Thereafter, the colony counts were determined, and the amount of antimicrobial present in the disks was determined by extracting the antimicrobial from the disk with alcohol, followed by spectrophotometric measurement. The results are shown in Table 6.

TABLE 6

| Solution | Drug levels (µg/disk) | Bacterial Adherence of S. aureus (CFU/cm) Day 5 |
|---|---|---|
| 70% (v/v) THF + 30% (v/v) methanol | 0 | >$10^5$ |
| 0.4% CHA in 70% (v/v) THF + 30% (v/v) methanol | 264 | 8 × $10^2$ |
| 0.4% CHX in 70% (v/v) THF + 30% (v/v) methanol | 361 | 1 × $10^2$ |
| 0.2% CHA + 0.2% CHX in 70% (v/v) THF + 30% (v/v) methanol | 360 | 60 |

These results demonstrate the synergistic effect of treating PTFE soft tissue patches with a solution comprising a mixture of CHX and CHA.

Various publications are cited herein, which are hereby incorporated by reference in their entireties.

We claim:

1. An antimicrobial medical article prepared by treating a hydrophobic polymeric medical article, for an effective period of time, with a solution consisting essentially of one or more solvents and a mixture of chlorhexidine free base and a water-soluble chlorhexidine salt, wherein the weight/weight ratio of chlorhexidine free base and the water-soluble chlorhexidine salt in the solution is between 1:1 to 1:5.

2. The antimicrobial medical article of claim 1, wherein the article is expanded polytetrafluoroethylene.

3. The antimicrobial medical article of claim 1, wherein the article is a polytetrafluoroethylene soft tissue patch.

4. A method of preparing a medical article comprising the steps of:
(i) placing the medical article in a solution consisting essentially of (a) a solvent selected from the group consisting of water, reagent alcohol, tetrahydrofuran, dimethylsulfoxide, dimethylformamide, N-methyl-2-pyrrolidone, and mixtures thereof; and (b) a mixture of chlorhexidine free base and a water-soluble chlorhexidine salt, wherein the weight/weight ratio of chlorhexidine free base and water-soluble chlorhexidine salt in the solution is between 1:1 to 1:5;
(ii) soaking the medical article in the solution for an effective period of time to allow the medical article to swell;
(iii) removing the medical article from the solution; and
(iv) drying the medical article.

5. The method of claim 4, wherein the medical article is a hydrophobic polymeric medical article.

6. The method of claim 5, wherein the hydrophobic polymeric medical article is selected from the group consisting of expanded polytetrafluoroethylene and a polytetrafluoroethylene soft tissue patch.

* * * * *